(12) United States Patent
Van Der Schaaf et al.

(10) Patent No.: US 6,858,643 B2
(45) Date of Patent: Feb. 22, 2005

(54) CRYSTALLINE FORMS OF FLUVASTATIN SODIUM

(75) Inventors: Paul Adriaan Van Der Schaaf, Allschwil (CH); Heinz Wolleb, Fehren (CH); Annemarie Wolleb, Fehren (CH); Claudia Marcolli, Zürich (CH); Martin Szelagiewicz, Münchenstein (CH); Andreas Burkhard, Basel (CH); Beat Freiermuth, Buschwiller (FR)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/130,043

(22) PCT Filed: Oct. 23, 2001

(86) PCT No.: PCT/EP01/12239

§ 371 (c)(1),
(2), (4) Date: Oct. 1, 2002

(87) PCT Pub. No.: WO02/36563

PCT Pub. Date: May 10, 2002

(65) Prior Publication Data

US 2003/0125569 A1 Jul. 3, 2003

(30) Foreign Application Priority Data

Oct. 31, 2000 (DE) ............................................ 00811013

(51) Int. Cl.$^7$ ........................ A61K 31/40; C07D 209/12
(52) U.S. Cl. ........................................ 514/419; 548/494
(58) Field of Search ........................... 514/419; 548/494

(56) References Cited

U.S. PATENT DOCUMENTS 4,739,073 A    4/1988  Kathawala ................... 548/406

FOREIGN PATENT DOCUMENTS

WO    97/49681    12/1997

OTHER PUBLICATIONS

O. Tempkin et al., Tetrahedron, vol. 53, No. 31, pp. 10659–10670 (1997).

*Primary Examiner*—Deborah C. Lambkin
(74) *Attorney, Agent, or Firm*—Kevin T. Mansfield (57) ABSTRACT

Crystalline forms of the (3R,5S)- and the (3S,5R)-enantiomers of fluvastatin, referred to as polymorphic Forms A, B1, B2, C, D and E, processes for the preparation of these crystalline forms and pharmaceutical compositions comprising them are disclosed.

22 Claims, 7 Drawing Sheets

CRYSTALLINE FORMS OF FLUVASTATIN SODIUM

The present invention is directed to crystalline forms of the (3R,5S)- and the (3S,5R)-enantiomer of fluvastatin sodium, processes for their preparation and pharmaceutical compositions comprising these crystalline forms.

Fluvastatin sodium is known by its chemical name 7-(3-(4-fluorophenyl)-1-(1-methylethyl)-1H-indol-2-yl)-3,5-dihydroxy-6-heptenoic acid monosodium salt. The (3R,5S)- and the (3S,5R)-enantiomer of Fluvastatin have the following formula:

(3R, 5S)-enantiomer (3S, 5R)-enantiomer

Fluvastatin is an inhibitor of 3-hydroxy-3-methylglutaryl coenzyme A (HMG-CoA) and is used to lower the blood cholesterol level.

Fluvastatin as racemate as well as the single enantiomers are disclosed in U.S. Pat. No. 4,739,073. The publication by O. Tempkin et al. in Tetrahedron 1997, vol. 53, pages 10659–10670 discloses the enantiomer having the (3R,5S) conformation of 7-(3-(4-fluorophenyl)-1-(1-methylethyl)-1H-indol-2-yl)-3,5-dihydroxy-6-heptenoic acid monosodium salt to be the biologically most potent enantiomer. The processes for the preparation of the (3R,5S)-enantiomer of Fluvastatin in the above mentioned patent and publication disclose the amorphous form which has unsuitable characteristics for large scale production and has an unsuitable stability. We have now surprisingly found that the (3R,5S)- and the (3S,5R)-enantiomer of Fluvastatin sodium can be prepared in crystalline form. A major advantage of these crystalline forms is that they are less hygroscopic than the amorphous form. Therefore, the crystalline forms can be better handled and are more stable at normal environmental humidity levels. Another advantage of these crystalline forms is that they can be obtained from aqueous media without the risk of residual organic solvents.

Thus the present invention provides Fluvastatin in new crystalline forms designated as Form A, Form B1, Form B2, Form C, Form D and Form E.

These new crystalline forms of the (3R,5S)- and the (3S,5R)-enantiomer of Fluvastatin sodium are novel hydrates and have water contents from 0 up to 8 molecules of water per molecule of Fluvastatin sodium, wherein a water content of 0 molecules stands for the dehydrated hydrate.

Accordingly, the present invention is directed to the following polymorphic forms of Fluvastatin sodium:

A crystalline polymorph of (3R,5S)- or (3S,5R)-7-(3-(4-fluorophenyl)-1-(1-methylethyl)-1H-indol-2-yl)-3,5-dihydroxy-6-heptenoic acid monosodium salt which exhibits a characteristic X-ray powder diffraction pattern with characteristic peaks expressed in d-values (Å):

22.6 (w), 7.9 (w), 7.4 (s), 6.9 (m), 6.2 (m), 5.52 (w), 5.04 (vs), 4.85 (vs), 4.72 (w), 4.46 (m), 4.30 (s), 4.09 (s), 3.93 (m), 3.73 (vw), 3.67 (w), 3.52 (w), 3.45 (w), 3.35 (w), 3.21 (m), 3.02 (w), 2.86 (w), 2.73 (vw), 2.64 (vw), 2.50 (vw), 2.44 (w), 2.35 (vw), 2.28 (vw), herein designated as Form E. Here and in the following the abbreviations in brackets mean:

(vs)=very strong intensity; (s)=strong intensity; (m)=medium intensity; (w)=weak intensity; and (vw)=very weak intensity.

A crystalline polymorph of (3R,5S)- or (3S,5R)-7-(3-(4-fluorophenyl)-1-(1-methylethyl)-1H-indol-2-yl)-3,5-dihydroxy-6-heptenoic acid monosodium salt which has characteristic Raman bands, expressed in wave number (cm$^{-1}$):

3067 (m), 2992 (w), 2945 (m), 2914 (m), 1656 (vs), 1602 (s), 1570 (m), 1537 (s), 1500 (s) 1458 (s), 1421 (m), 1387 (m), 1360 (w), 1339 (m), 1299 (m), 1237 (w), 1209 (m), 1159 (w), 1141 (w), 1118 (w), 1072 (w), 1023 (w), 969 (w), 943 (w), 917 (w), 891 (w), 847 (w), 815 (m), 775 (w), 757 (w), 719 (w), 695 (w), 633 (w), 605 (w), 565 (w), 532 (w), 423 (w), 391 (w), 351 (w), 278 (w), 191 (m);

herein designated as Form E.

A crystalline polymorph of (3R,5S)- or (3S,5R)-7-(3-(4-fluorophenyl)-1-(1-methylethyl)-1H-indol-2-yl)-3,5-dihydroxy-6-heptenoic acid monosodium salt which exhibits a characteristic X-ray powder diffraction pattern with characteristic peaks expressed in d-values (Å):

24.2 (m), 12.4 (vw), 9.1 (vw), 8.2 (s), 7.1 (m), 6.0 (vw), 5.54 (w), 5.17 (vw), 4.90 (m), 4.73 (m), 4.08 (m), 3.48 (vw), 2.98 (vw), herein designated as Form A.

A crystalline polymorph of (3R,5S)- or (3S,5R)-7-(3-(4-fluorophenyl)-1-(1-methylethyl)-1H-indol-2-yl)-3,5-dihydroxy-6-heptenoic acid monosodium salt which exhibits a characteristic X-ray powder diffraction pattern with characteristic peaks expressed in d-values (Å):

25.2 (w), 12.1 (vw), 8.6 (m), 8.1 (m), 7.1 (w), 6.4 (vw), 5.99 (w), 5.69 (vw), 5.57 (w), 5.22 (w), 4.93 (s), 4.78 (s), 4.50 (w), 4.30 (vw), 4.12 (s), 3.80 (m), 3.71 (vw), 3.46 (w), 3.34 (w), 3.23 (vw), 2.97 (w), herein designated as Form B1.

A crystalline polymorph of (3R,5S)- or (3S,5R)-7-(3-(4-fluorophenyl)-1-(1-methylethyl)-1H-indol-2-yl)-3,5-dihydroxy-6-heptenoic acid monosodium salt which exhibits a characteristic X-ray powder diffraction pattern with characteristic peaks expressed in d-values (Å):

26.5 (w), 13.3 (vw), 12.1 (vw), 8.8 (m), 8.1 (w), 7.3 (w), 7.1 (w), 6.6 (w), 6.0 (w), 5.74 (vw), 5.60 (w), 5.27 (w), 4.96 (s), 4.81 (s), 4.57 (w), 4.41 (w), 4.35 (vw), 4.14 (s), 4.05 (vw), 3.81 (w), 3.74 (vw), 3.47 (w), 3.36 (w), 3.22 (vw), 3.15 (vw), 2.98 (w), 2.80 (vw), 2.75 (vw), 2.59 (vw), herein designated as Form B2.

A crystalline polymorph of (3R,5S)- or (3S,5R)-7-(3-(4-fluorophenyl)-1-(1-methylethyl)-1H-indol-2-yl)-3,5- dihydroxy-6-heptenoic acid monosodium salt which exhibits a characteristic X-ray powder diffraction pattern with characteristic peaks expressed in d-values (Å):

27.5 (w), 13.8 (vw), 9.3 (m), 8.6 (w), 8.1 (w), 7.4 (w), 7.1 (vw), 6.9 (s), 6.1 (w), 5.57 (vw), 5.19 (vw), 4.97 (vs), 4.75 (s), 4.62 (m), 4.13 (m), 4.04 (m), 3.97 (w), 3.82 (vw), 3.76 (vw), 3.66 (vw), 3.53 (w), 3.33 (w), 3.08 (w), 2.99 (vw), herein designated as Form C.

A crystalline polymorph of (3R,5S)- or (3S,5R)-7-(3-(4-fluorophenyl)-1-(1-methylethyl)-1H-indol-2-yl)-3,5-dihydroxy-6-heptenoic acid monosodium salt which exhibits a characteristic X-ray powder diffraction pattern with characteristic peaks expressed in d-values (Å):

30.1 (w), 10.0 (w), 8.6 (w), 8.3 (w), 7.5 (s), 6.5 (w), 6.2 (vw), 6.0 (m), 5.01 (s), 4.83 (m), 4.31 (w), 4.13 (m), 3.95 (w), 3.54 (w), 3.44 (vw), 3.00 (w).

herein designated as Form D.

A discussion of the theory of X-ray powder diffraction patterns can be found in "X-ray diffraction procedures" by H. P. Klug and L. E. Alexander, J. Wiley, New York (1974).

The above crystalline polymorphs either are the (3R,5S)-enantiomer or the (3S,5R)-enantiomer; the crystalline polymorphs of the (3R,5S)-enantiomer are preferred.

Enantiomers have the same solid state properties, like X-ray and Raman data (see for example Z. Jane Li et al., J. Pharm. Sci., 1999, 88, pages 337–346).

Furthermore, the present invention is directed to processes for the preparation of Forms A, B1, B2, C, D and E.

Form E can be prepared by treating an aqueous solution of the (3R,5S)- or (3S,5R)-enantiomer of Fluvastatin sodium in order to effect at least minimal precipitation of the compound, followed by freeze drying of the suspension or of the precipitated compound.

Precipitation of Fluvastatin sodium can, for example, be effected by concentrating or cooling of the aqueous solution.

A process wherein the aqueous solution is cooled and subsequently the precipitated compound is freeze dried is preferred. For example, at a temperature of 30 to 80° C., especially 40 to 60° C., an aqueous solution can be prepared which is then cooled to a temperature of 0 to 15° C., especially about 0° C., in order to effect precipitation of the compound.

According to an alternative process for the preparation of Form E precipitation of Fluvastatin sodium can be effected to an extent that the resulting suspension has a turbid appearance and then the suspension itself is freeze dried. For this process it is preferred that precipitation is effected in such a way that the solution is concentrated, especially by evaporation of the water in vacuum.

In all of the above processes freeze drying can be carried out according to known methods.

The preparation of crystalline polymorphic Forms A, B1, B2, C and D is usually carried out by using Form E as the starting compound and by exposing Form E to an atmosphere having a defined relative humidity. Depending on the relative humidity used the different forms can be obtained.

For Form A it is preferred to use a relative humidity of 0 to 20%.

For Forms B1 and B2 it is preferred to use a relative humidity of 20 to 60%, especially 20 to 55%.

For Form C it is preferred to use a relative humidity of 60 to 75%, especially 65 to 75%.

For Form D it is preferred to use a relative humidity of at least 75%, especially about 90%.

For the preparation of Forms A, B1, B2, C and D it is preferred to carry out in advance to the exposure to an atmosphere of defined relative humidity an exposure to an atmosphere having a relative humidity of at least 75%, preferably at least 80% and most preferably about 90%.

Another object of the present invention are pharmaceutical compositions comprising an effective amount of crystalline polymorphic Form A, B1, B2, C, D or E, and a pharmaceutically acceptable carrier.

The polymorphic forms may be used as single components or mixtures.

As to pharmaceutical compositions of Fluvastatin sodium it is preferred that these contain 25–100% by weight, especially 50–100% by weight, of at least one of the novel forms, based on the total amount of Fluvastatin sodium. Preferably, such an amount of the novel polymorphic forms of Fluvastatin sodium is 75–100% by weight, especially 90–100% by weight. Highly preferred is an amount of 95–100% by weight.

The following examples will illustrate, but do not limit the scope of the present invention.

EXAMPLE 1

Figure 6:
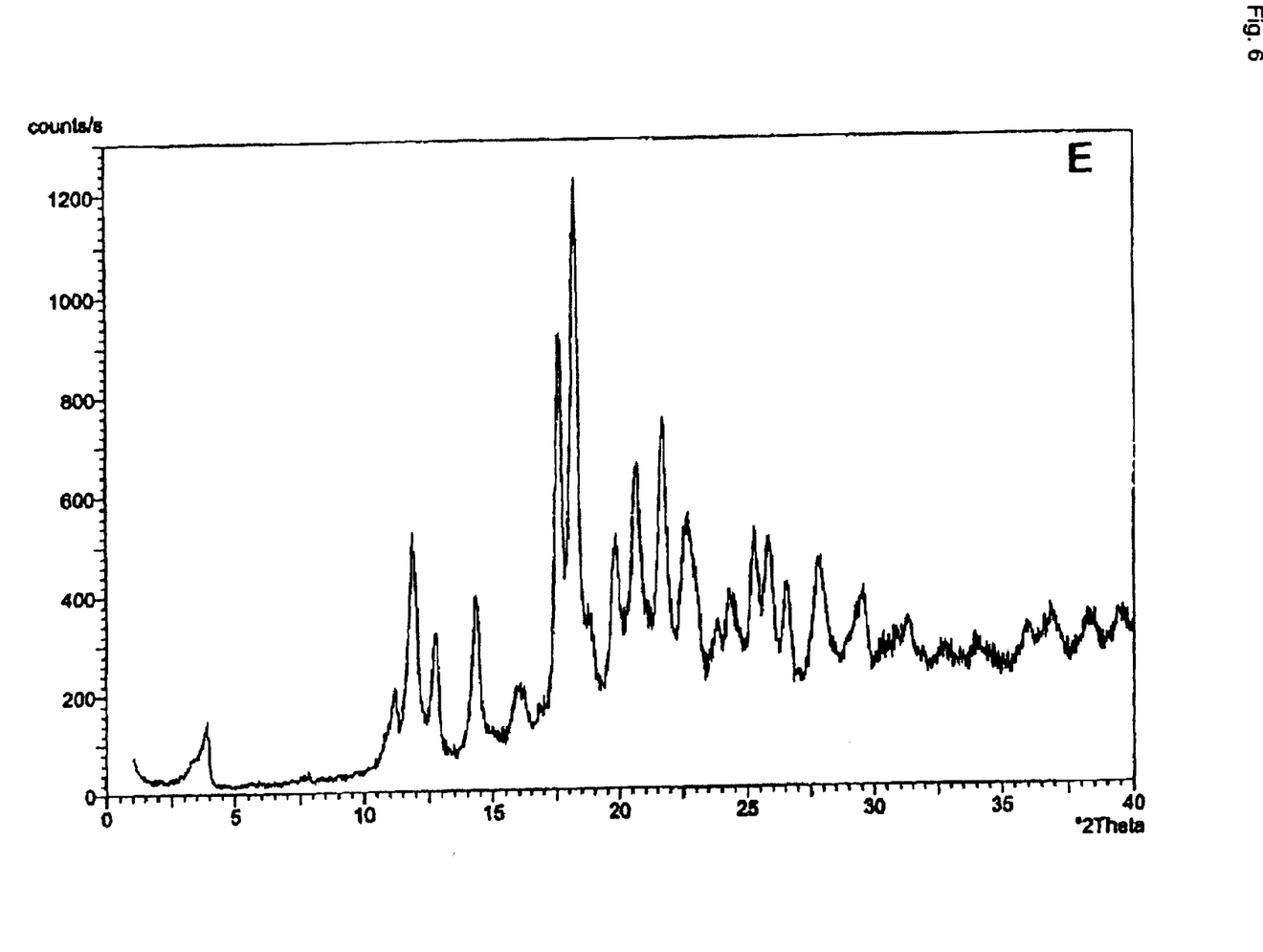
FIG. 6 is a characteristic X-ray powder diffraction pattern for Form E
Figure 7A:
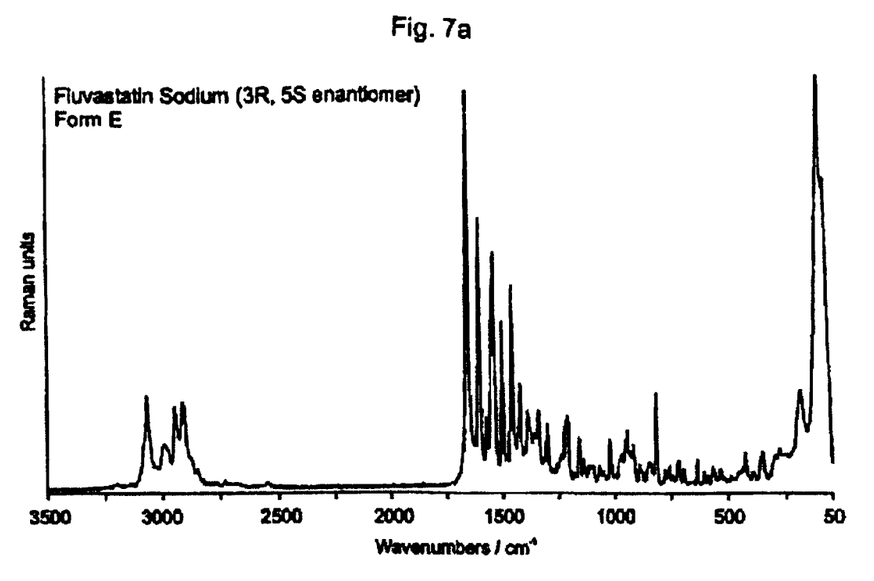
FIG. 7a is a characteristic Raman spectrum of Form E of the (3R,5S)-enantiomer

Preparation of Polymorphic Form E 700 parts water are added to 70 parts Fluvastatin sodium ((3R,5S)-enantiomer). The suspension is heated up to 50° C. until a clear solution is formed. The solution is chilled in an ice bath and the precipitated product is equilibrated for 3 hours at approximately 0° C. The suspension is subsequently freeze dried. X-ray powder diffraction studies show the product to be polymorphic Form E (see FIGS. 6 and 7a).

Figure 7B:
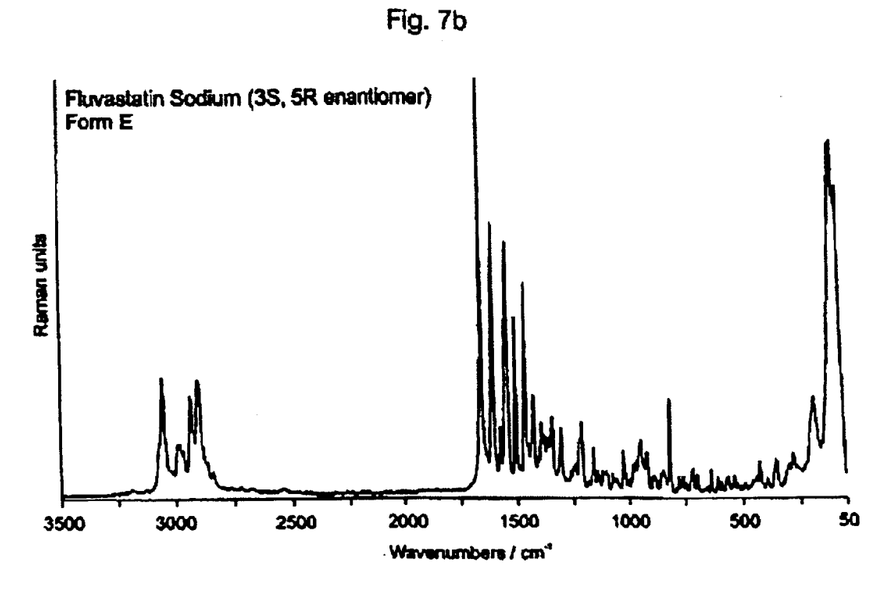
FIG. 7b is a characteristic Raman spectrum of Form E of the (3S,5R)-enantiomer

Following the procedure given above but replacing the (3R,5S)-enantiomer with the corresponding (3S,5R)-enantiomer leads to Form E of the (3S,5R)-enantiomer (see FIG. 7b).

EXAMPLE 2

Preparation of Polymorphic Form A

Figure 1:
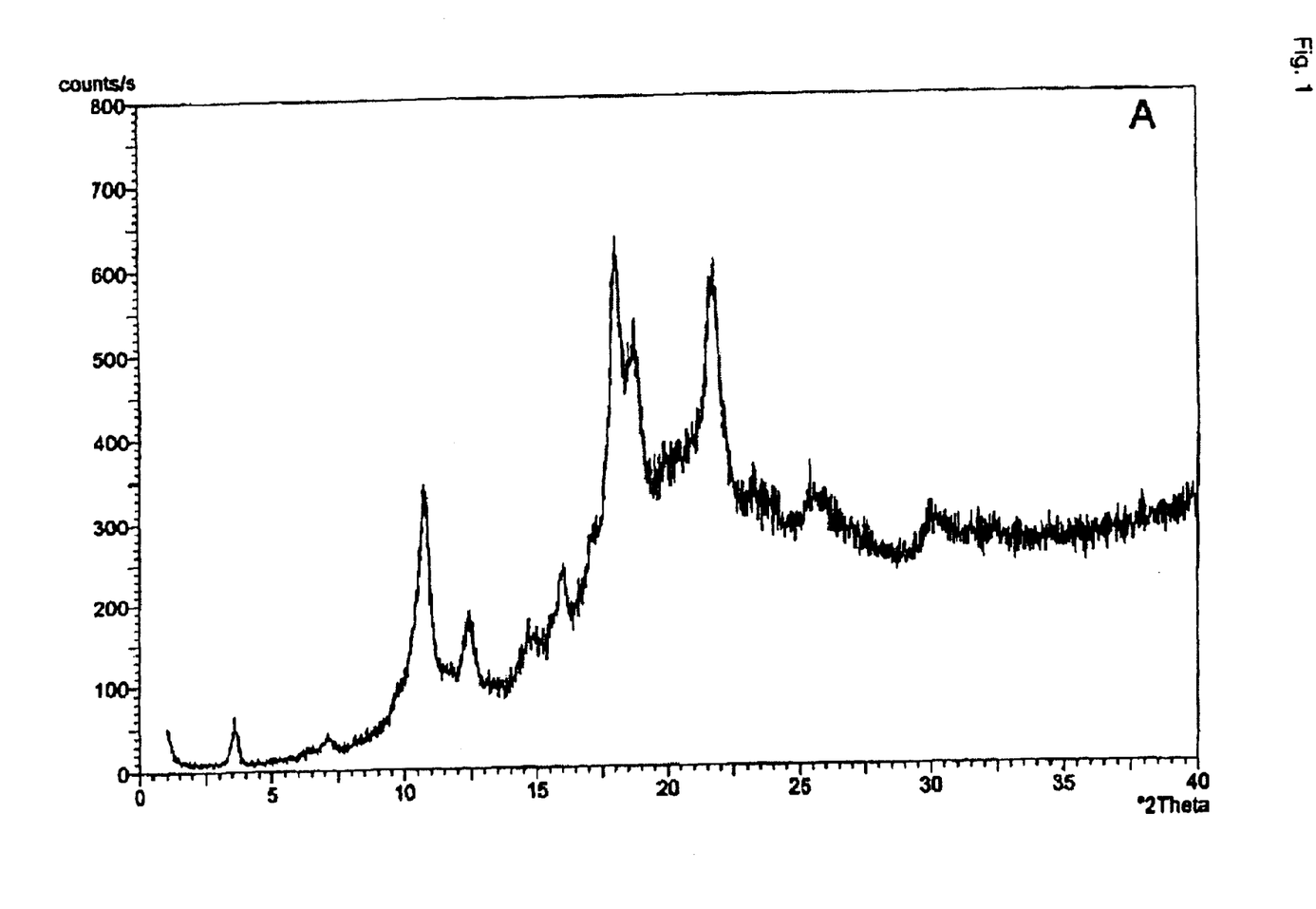
FIG. 1 is a characteristic X-ray powder diffraction pattern for Form A

Form E of Fluvastatin sodium ((3R,5S)-enantiomer) is first exposed to an atmosphere having a relative humidity of 90% for about 4 hours and subsequently to an atmosphere of 0 to 20% for about 90 minutes. This treatment leads to Form A of the (3R,5S)-enantiomer with an estimated water content of 0 to 5%. The above treatment can be carried out in an X-ray diffractometer in which the relative humidity of the atmosphere can be controlled during the measurement. X-ray powder diffraction studies show the product to be polymorphic Form A (see FIG. 1).

Following the procedure given above but replacing Form E of the (3R,5S)-enantiomer with Form E of the (3S,5R)-enantiomer leads to Form A of the (3S,5R)-enantiomer.

EXAMPLE 3

Preparation of Polymorphic Forms B1 and B2

Figure 2:
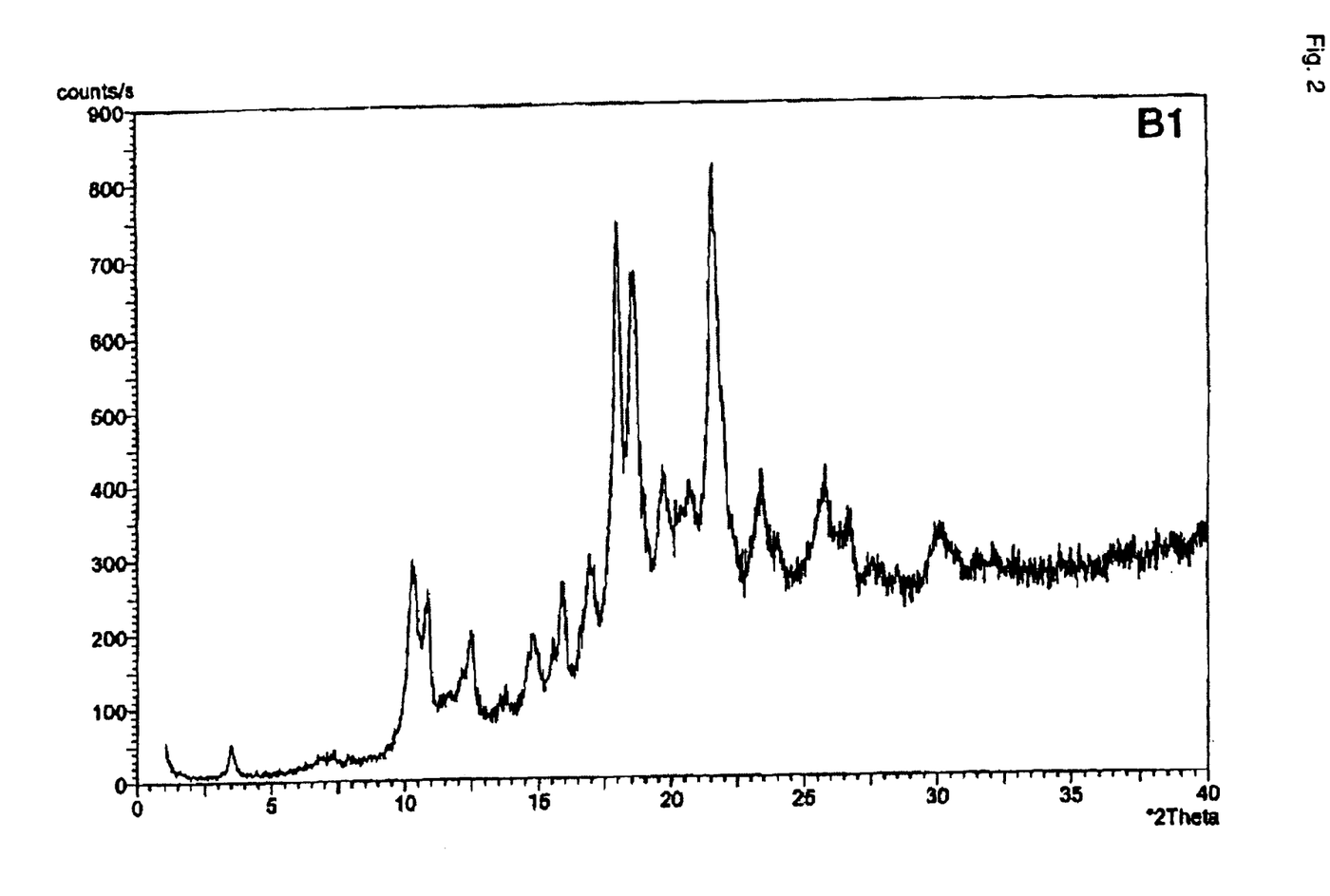
FIG. 2 is a characteristic X-ray powder diffraction pattern for Form B1
Figure 3:
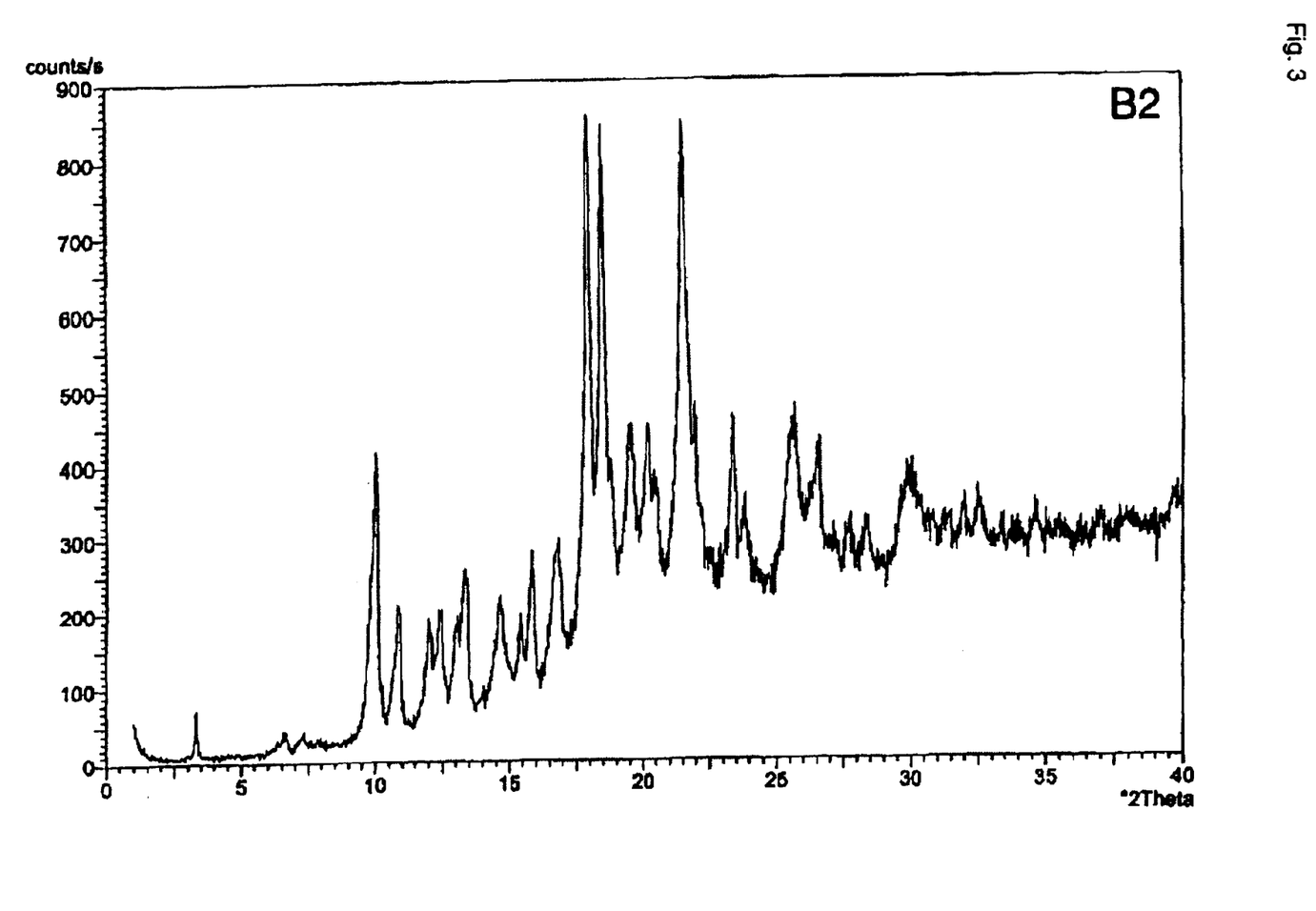
FIG. 3 is a characteristic X-ray powder diffraction pattern for Form B2

Form E of Fluvastatin sodium ((3R,5S)-enantiomer) is first exposed to an atmosphere having a relative humidity of 90% for about 4 hours and subsequently to an atmosphere of 20 to 55% for about 3 hours. This treatment leads to either Form B1 or Form B2 of the (3R,5S)-enantiomer with an estimated water content of 5 to 15%. The above treatment can be carried out in an X-ray diffractometer in which the relative humidity of the atmosphere can be controlled during the measurement. X-ray powder diffraction studies show the product to be polymorphic Form B1 (see FIG. 2) or polymorphic Form B2 (see FIG. 3).

Following the procedure given above but replacing Form E of the (3R,5S)-enantiomer with Form E of the (3S,5R)-enantiomer leads to either Form B1 or Form B2 of the (3S,5R)-enantiomer.

EXAMPLE 4
Preparation of Polymorphic Form C

Figure 4:
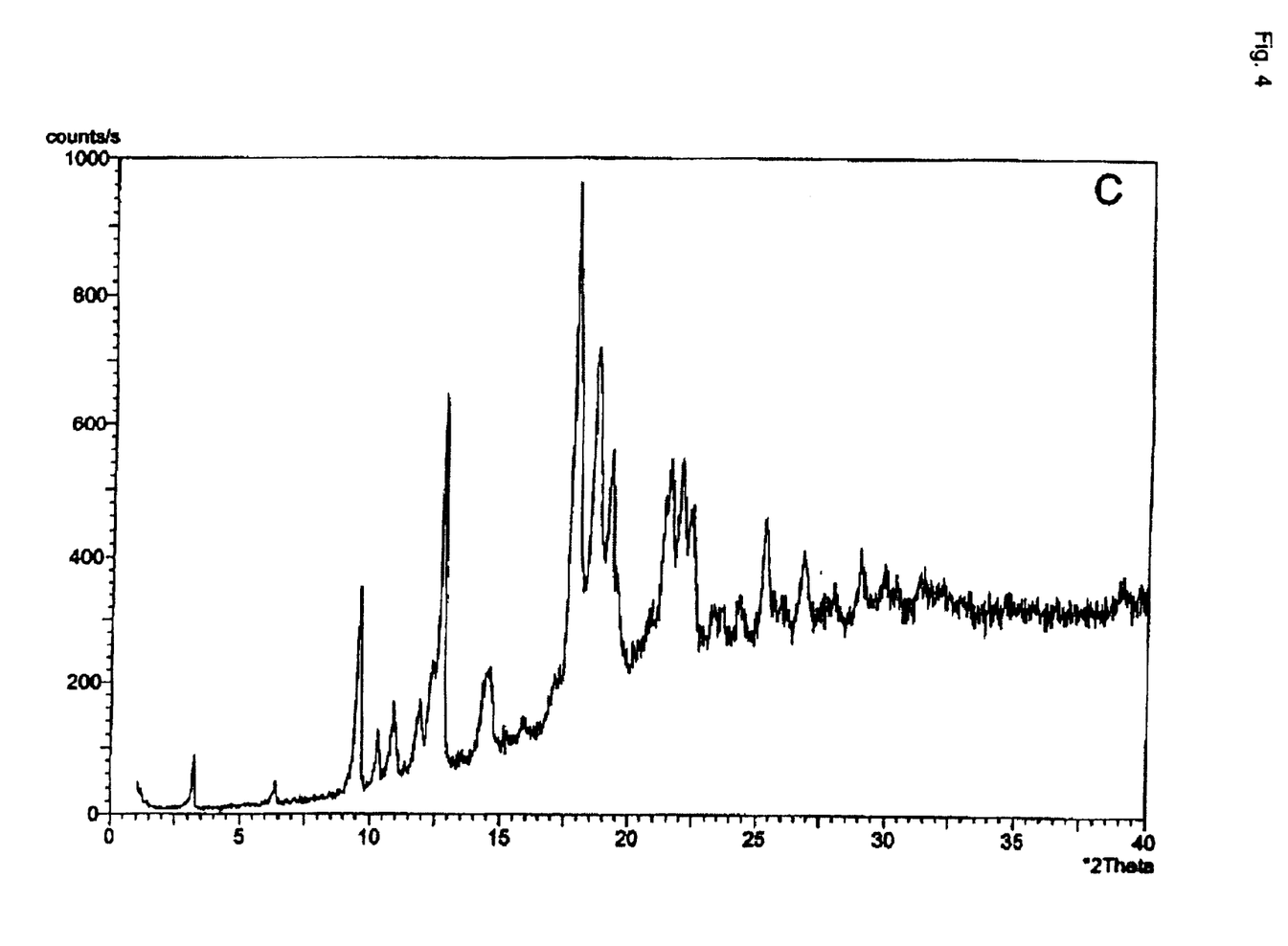
FIG. 4 is a characteristic X-ray powder diffraction pattern for Form C

Form E of Fluvastatin sodium ((3R,5S)-enantiomer) is exposed to an atmosphere having a relative humidity of 75% for about 13 hours. This treatment leads to Form C of the (3R,5S)-enantiomer with an estimated water content of 20 to 25%. The above treatment can be carried out in an X-ray diffractometer in which the relative humidity of the atmosphere can be controlled during the measurement. X-ray powder diffraction studies show the product to be polymorphic Form C (see FIG. 4).

Following the procedure given above but replacing Form E of the (3R,5S)-enantiomer with Form E of the (3S,5R)-enantiomer leads to Form C of the (3S,5R)-enantiomer.

EXAMPLE 5
Preparation of Polymorphic Form D

Figure 5:
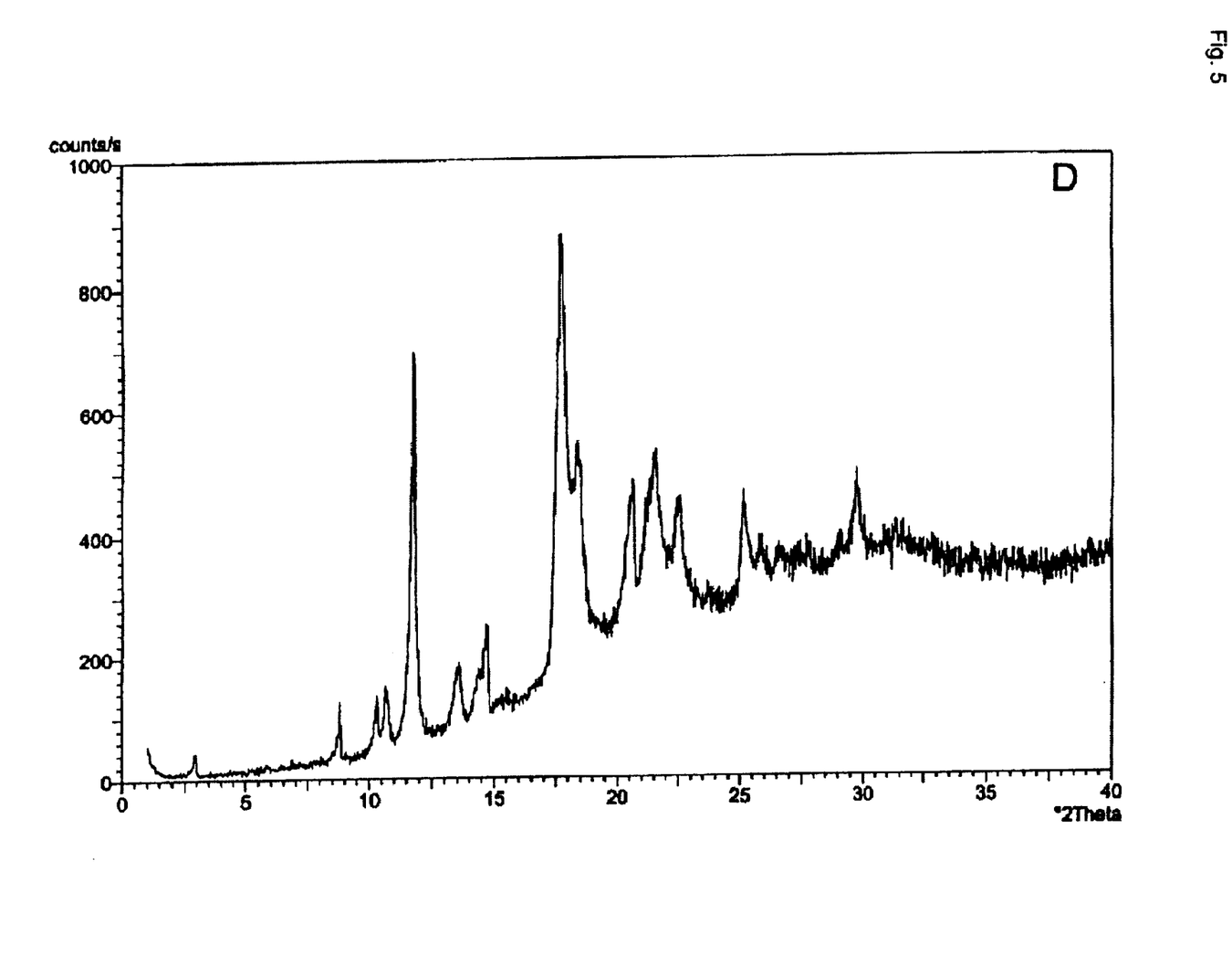
FIG. 5 is a characteristic X-ray powder diffraction pattern for Form D

Form E of Fluvastatin sodium ((3R,5S)-enantiomer) is exposed to an atmosphere having a relative humidity of 90% for about 4 hours. This treatment leads to Form D of the (3R,5S)-enantiomer with an estimated water content of 30%. The above treatment can be carried out in an X-ray diffractometer in which the relative humidity of the atmosphere can be controlled during the measurement. X-ray powder diffraction studies show the product to be polymorphic Form D (see FIG. 5).

Following the procedure given above but replacing Form E of the (3R,5S)-enantiomer with Form E of the (3S,5R)-enantiomer leads to Form D of the (3S,5R)-enantiomer.

What is claimed is:

1. A crystalline polymorph of (3R,5S)- or (3S,5R)-7-(3-(4-fluorophenyl)-1-(1-methylethyl)-1H-indol-2-yl)-3,5-dihydroxy-6-heptenoic acid monosodium salt which exhibits a characteristic X-ray powder diffraction pattern with characteristic peaks expressed in d-values (Å):

22.6 (w), 7.9 (w), 7.4 (s), 6.9 (m), 6.2 (m), 5.52 (w), 5.04 (vs), 4.85 (vs), 4.72 (w), 4.46 (m), 4.30 (s), 4.09 (s), 3.93 (m), 3.73 (vw), 3.67 (w), 3.52 (w), 3.45 (w), 3.35 (w), 3.21 (m), 3.02 (w), 2.86 (w), 2.73 (vw), 2.64 (vw), 2.50 (vw), 2.44 (w), 2.35 (vw), 2.28 (vw), wherein (vs)=very strong intensity; (s)=strong intensity; (m)=medium intensity; (w)=weak intensity; and (vw)=very weak intensity.

2. A crystalline polymorph of (3R,5S)- or (3S,5R)-7-(3-(4-fluorophenyl)-1-(1-methylethyl)-1H-indol-2-yl)-3,5-dihydroxy-6-heptenoic acid monosodium salt according to claim 1, which has characteristic Raman bands, expressed in wave number (cm$^{-1}$): 3067 (m), 2992 (w), 2945 (m), 2914 (m), 1656 (vs)1602 (s), 1570 (m), 1537 (s), 1500 (s), 1458 (s), 1421 (m), 1387 (m), 1360 (w), 1339 (m), 1299 (m), 1237 (w), 1209 (m), 1159 (w), 1141 (w), 1118 (w), 1072 (w), 1023 (w), 969 (w), 943 (w), 917 (w), 891 (w), 847 (w), 815 (m), 775 (w), 757 (w), 719 (w), 695 (w), 633 (w), 605 (w), 565 (w), 532 (w), 423 (w), 391 (w), 351 (w), 278 (w), 191 (w); wherein (vs)=very strong intensity; (s)=strong intensity; (m)=medium intensity; and (w)=weak intensity.

3. A crystalline polymorph of (3R,5S)- or (3S,5R)-7-(3-(4-fluorophenyl)-1(1-methylethyl)-1H-indol-2-yl)-3,5-dihydroxy-6-heptenoic acid monosodium salt which exhibits a characteristic X-ray powder diffraction pattern with characteristic peaks expressed in d-values (Å):

24.2 (m), 12.4 (vw), 9.1 (vw), 8.2 (s), 7.1 (m), 6.0 (vw), 5.54 (w), 5.17 (vw), 4.90 (m), 4.73 (m), 4.08 (m), 3.48 (vw), 2.98 (vw), wherein (s)=strong intensity; (m)=medium intensity; (w)=weak intensity; and (vw)=very weak intensity.

4. A crystalline polymorph of (3R,5S)- or (3S,5R)-7-(3-(4-fluorophenyl)-1-(1-methylethyl)-1H-indol-2-yl)-3,5-dihydroxy-6-heptenoic acid monosodium salt which exhibits a characteristic X-ray powder diffraction pattern with characteristic peaks expressed in d-values (Å):

25.2 (w), 12.1 (vw), 8.6 (m), 8.1 (m), 7.1 (w), 6.4 (vw), 5.99 (w), 5.69 (vw), 5.57 (w), 5.22 (w), 4.93 (s), 4.78 (s), 4.50 (w), 4.30 (vw), 4.12 (s), 3.80 (m), 3.71 (vw), 3.46 (w), 3.34 (w), 3.23 (vw), 2.97 (w), wherein (s)=strong intensity; (m)=medium intensity; (w)=weak intensity; and (vw)=very weak intensity.

5. A crystalline polymorph of (3R,5S)- or (3S,5R)-7-(3-(4-fluorophenyl)-1-(1-methylethyl)-1H-indol-2-yl)-3,5-dihydroxy-6-heptenoic acid monosodium salt which exhibits a characteristic X-ray powder diffraction pattern with characteristic peaks expressed in d-values (Å):

26.5 (w), 13.3 (vw), 12.1 (vw), 8.8 (m), 8.1 (w), 7.3 (w), 7.1 (w), 6.6 (w), 6.0 (w), 5.74 (vw), 5.60 (w), 5.27 (w), 4.96 (a), 4.81 (s), 4.57 (w), 4.41 (w), 4.35 (vw), 4.14 (s), 4.05 (vw), 3.81 (w), 3.74 (vw), 3.47 (w), 3.36 (w), 3.22 (vw), 3.15 (vw), 2.98 (w), 2.80 (vw), 2.75 (vw), 2.59 (vw), wherein (s)=strong intensity; (m)=medium intensity; (w)=weak intensity; and (vw)=very weak intensity.

6. A crystalline polymorph of (3R,5S)- or (3S,5R)-7-(3-(4-fluorophenyl)-1-(1-methylethyl-1H-indol-2-yl)-3,5-dihydroxy-6-heptenoic acid monosodium salt which exhibits a characteristic X-ray powder diffraction pattern with characteristic peaks expressed in d-values (Å):

27.5 (w), 13.8 (vw), 9.3 (m), 8.6 (w), 8.1 (w), 7.4 (w), 7.1 (vw), 6.9 (s), 6.1 (w), 5.57 (vw), 5.19 (vw), 4.97 (vs), 4.75 (a), 4.62 (m), 4.13 (m), 4.04 (m), 3.97 (w), 3.82 (vw), 3.76 (vw), 3.66 (vw), 3.53 (vw), 3.33 (w), 3.08 (w), 2.99 (vw), wherein (vs)=very strong intensity; (s)=strong intensity; (m)=medium intensity; (w)=weak intensity; and (vw)=very weak intensity.

7. A crystalline polymorph of (3R,5S)- or (3S,5R)-7-(3-(4-fluorophenyl)-1-(1-methylethyl)-1H-indol-2-yl)-3,5-dihydroxy-6-heptenoic acid monosodium salt which exhibits a characteristic X-ray powder diffraction pattern with characteristic peaks expressed in d-values (Å):

30.1 (w), 10.0 (w), 8.6 (w), 8.3 (w), 7.5 (s), 6.5 (w), 6.2 (vw), 6.0 (m), 5.01 (s), 4.83 (m), 4.31 (w), 4.13 (m), 3.95 (w), 3.54 (w), 3.44 (vw), 3.00 (w), wherein (a)=strong intensity; (m)=medium intensity; (w)=weak intensity; and (vw)=very weak intensity.

8. A crystalline polymorph according to any of claims 1 to 7 which is the crystalline polymorph of (3R,5S)-7-(3-(4-fluorophenyl)-1-(1-methylethyl)-1H-indol-2-yl)-3,5-dihydroxy-6-heptenoic acid monosodium salt.

9. A crystalline polymorph according to any of claims 1 to 7 which is the crystalline polymorph of (3S,5R)-7-(3-(4-fluorophenyl)-1-(1-methylethyl)-1H-indol-2-yl)-3,5-dihydroxy-6-heptenoic acid monosodium salt.

10. A process for the preparation of a crystalline polymorph according to claim 1, which comprises treating an aqueous solution of (3R,5S)- or (3S,5R)-7-(3-(4-fluorophenyl)-1-(1-methylethyl)-1H-indol-2-yl)-3,5-dihydroxy-6-heptenoic acid monosodium salt in order to effect at least minimal precipitation of the compound, followed by freeze drying of the suspension or of the precipitated compound.

11. A process according to claim 10, wherein the aqueous solution is cooled and subsequently the precipitated compound is freeze dried.

12. A process according to claim 11, wherein seeding crystals are added to the solution.

13. A process according to claim 11, wherein the aqueous solution is prepared at a temperature of 30 to 80° C. and is cooled to a temperature of 0 to 15° C. in order to effect precipitation of the compound.

14. A process for the preparation of a crystalline polymorph according to any of claims 3 to 7, which comprises exposing a crystalline polymorph of (3R,5S)- or (3S,5R)-7-(3-(4-fluorophenyl)-1-(1-methylethyl)-1H-indol-2-yl)-3,5-dihydroxy-6-heptenoic acid monosodium salt which exhibits a characteristic X-ray powder diffraction pattern with characteristic peaks expressed in d-values (Å):

22.6 (w), 7.9 (w), 7.4 (s), 6.9 (m), 6.2 (m), 5.52 (w), 5.04 (vs), 4.85 (vs), 4.72 (w), 4.46 (m), 4.30 (s), 4.09 (s), 3.93 (m), 3.73 (vw), 3.67 (w), 3.52 (w), 3.45 (w), 3.35 (w), 3.21 (m), 3.02 (w), 2.86 (w), 2.73 (vw), 2.64 (vw), 2.50 (vw), 2.44 (w), 2.35 (vw), 2.28 (vw), wherein (vs)=very strong intensity; (s)=strong intensity; (m)=medium intensity; (w)=weak intensity; and (vw)=very weak intensity to an atmosphere having a defined relative humidity.

15. A process according to claim 14 for the preparation of a crystalline polymorph of (3R,5S)- or (3S,5R)-7-(3-(4-fluorophenyl)-1-(1-methylethyl)-1H-indol-2-yl)-3,5-dihydroxy-6-heptenoic acid monosodium salt which exhibits a characteristic X-ray powder diffraction pattern with characteristic peaks expressed in d-values (Å): 24.2 (m), 12.4 (vw), 9.1 (vw), 8.2 (s), 7.1 (m), 6.0 (vw), 5.54 (w), 5.17 (vw), 4.90 (m), 4.73 (m), 4.08 (m), 3.48 (vw), 2.98 (vw), wherein Cs)=strong intensity; (m)=medium intensity; (w)=weak intensity; and (vw)=very weak intensity, wherein the relative humidity is 0 to 20%.

16. A process according to claim 14 for the preparation of a crystalline polymorph of (3R,5S)- or (3S,5R)-7-(3-(4-fluorophenyl)-1-(1-methylethyl)-1H-indol-2-yl)-3,5-dihydroxy-6-heptenoic acid monosodium salt which exhibits a characteristic X-ray powder diffraction pattern with characteristic peaks expressed in d-values (Å):

25.2 (w), 12.1 (vw), 8.6 (m), 8.1 (m), 7.1 (w), 6.4 (vw), 5.99 (w), 5.69 (vw), 5.57 (w), 5.52 (w), 4.93 (s), 4.78 (s), 4.50 (w), 4.30 (vw), 4.12 (s), 3.80 (m), 3.71 (vw), 3.46 (w), 3.34 (w), 3.23 (vw), 2.97 (w), wherein (s)=strong intensity; (m)=medium intensity; (w)=weak intensity; and (vw)=very weak intensity, wherein the relative humidity is 20 to 60%.

17. A process according to claim 14 for the preparation of a crystalline polymorph of (3R,5S)- or (3S,5R)-7-(3-(4-fluorophenyl)-1-(1-methylethyl)-1H-indol-2-yl)-3,5-dihydroxy-6-heptenoic acid monosodium salt which exhibits a characteristic X-ray powder diffraction pattern with characteristic peaks expressed in d-values (Å):

27.5 (w), 13.8 (vw), 9.3 (m), 8.6 (w), 8.1 (w), 7.4 (w), 7.1 (vw), 6.9 (s), 6.1 (w), 5.57 (vw), 5.19 (vw), 4.97 (vs), 4.75 (s), 4.62 (m), 4.13 (m), 4.04 (m), 3.97 (w), 3.82 (vw), 3.76 (vw), 3.66 (vw), 3.53 (w), 3.33 (w), 3.08 (w), 2.99 (vw), wherein (vs)=very strong intensity; (s)=strong intensity; (m)=medium intensity; (w)=weak intensity; and (vw)=very weak intensity, wherein the relative humidity is 60 to 75%.

18. A process according to claim 14 for the preparation of a crystalline polymorph of (3R,5S)- or (3S,5R)-7-(3-(4-fluorophenyl)-1-(1-methylethyl)-1H-indol-2-yl)-3,5-dihydroxy-6-heptenoic acid monosodium salt which exhibits a characteristic X-ray powder diffraction pattern with characteristic peaks expressed in d-values (Å): 30.1 (w), 10.0 (w), 8.6 (w), 8.3 (w), 7.5 (s), 6.5 (w), 6.2 (vw), 6.0 (m), 5.01 (s), 4.83 (m), 4.31 (w), 4.13 (m), 3.95 (w), 3.54 (w), 3.44 (vw), 3.00 (w), wherein (s)=strong intensity; (m)=medium intensity; (w)=weak intensity; and (vw)=very weak intensity, wherein the relative humidity is at least 75%.

19. A process according to claim 14 wherein, in advance to the exposure to an atmosphere of defined relative humidity, an exposure to an atmosphere having a relative humidity of at least 75% is carried out.

20. A pharmaceutical composition comprising an effective amount of a crystalline polymorphic form according to any of claims 1 to 7, and a pharmaceutically acceptable carrier.

21. A process according to claim 12, wherein seeding crystals are added to the solution before cooling of said solution.

22. A process according to claim 14 for the preparation of a crystalline polymorph of (3R,5S)- or (3S,5R)-7-(3-(4-fluorophenyl)-1-(1-methylethyl)-1H-indol-2-yl)-3,5-dihydroxy-6-heptenoic acid monosodium salt which exhibits a characteristic X-ray powder diffraction pattern with characteristic peaks expressed in d-values (Å): 26.5 (w), 13.3 (vw), 12.1 (vw), 8.8 (m), 8.1 (w), 7.3 (w), 7.1 (w), 6.6 (w), 6.0 (w), 5.74 (vw), 5.60 (w), 5.27 (w), 4.96 (s), 4.81 (s), 4.57 (w), 4.41 (w), 4.35 (vw), 4.14 (s), 4.05 (vw), 3.81 (w), 3.74 (vw), 3.47 (w), 3.36 (w), 3.22 (vw), 3.15 (vw), 2.98 (w), 2.80 (vw), 2.75 (vw), 2.59 (vw), wherein (s)=strong intensity; (m)=medium intensity; (w)=weak intensity; and (vw)=very weak intensity, wherein the relative humidity is 20 to 60%.

* * * * *